United States Patent
Asp et al.

(10) Patent No.: US 7,993,314 B2
(45) Date of Patent: Aug. 9, 2011

(54) ABSORBENT ARTICLE HAVING A POCKET FOR RECEIVING AND STORING FAECES AND METHOD FOR ITS MANUFACTURE

(75) Inventors: Fredrik Asp, Onsala (SE); Marie Johansson, Mölnlycke (SE); Filip Jansson, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 11/819,728

(22) Filed: Jun. 28, 2007

(65) Prior Publication Data

US 2007/0255245 A1 Nov. 1, 2007

Related U.S. Application Data

(63) Continuation of application No. PCT/SE2004/002027, filed on Dec. 29, 2004.

(51) Int. Cl.
*A61F 5/44* (2006.01)
*A61F 13/20* (2006.01)
*A61F 13/15* (2006.01)

(52) U.S. Cl. .............. 604/348; 604/385.24; 604/385.01; 604/385.19

(58) Field of Classification Search ............. 604/385.19, 604/385.01
See application file for complete search history.

(56) References Cited

U.S. PATENT DOCUMENTS

| | | | |
|---|---|---|---|
| 2,043,325 A | 6/1936 | Jackson, Jr. | |
| 4,642,110 A | 2/1987 | Dudek | |
| 5,062,840 A * | 11/1991 | Holt et al. | 604/385.19 |
| 5,176,672 A * | 1/1993 | Bruemmer et al. | 604/385.19 |
| 5,624,422 A * | 4/1997 | Allen | 604/385.23 |
| 5,792,130 A | 8/1998 | Widlund et al. | |
| 6,248,098 B1 | 6/2001 | Sayama | |
| 6,346,097 B1 | 2/2002 | Blaney | |
| 6,402,728 B2 * | 6/2002 | Otsubo | 604/385.19 |
| 6,402,729 B1 | 6/2002 | Boberg et al. | |
| 6,527,756 B1 * | 3/2003 | Mishima et al. | 604/385.19 |
| 6,758,838 B2 * | 7/2004 | Mishima et al. | 604/385.08 |
| 6,869,423 B2 * | 3/2005 | Onishi et al. | 604/385.01 |

(Continued)

FOREIGN PATENT DOCUMENTS

EP 0 613 671 A2 9/1994

(Continued)

OTHER PUBLICATIONS

Machine Translation of JP 2003038553, Japanese publication date Feb. 12, 2003.*

(Continued)

*Primary Examiner* — Leslie R Deak
*Assistant Examiner* — Susan Su
(74) *Attorney, Agent, or Firm* — Buchanan Ingersoll & Rooney PC

(57) ABSTRACT

An absorbent article, such as an incontinence shield, diaper, pant-diaper, belt diaper or the like, includes a topsheet, a backsheet and an absorbent core placed therebetween. The absorbent core has two longitudinal edges, and a front and a rear transverse edge, wherein the rear transverse edge possesses a recess with at least one pair of opposing edges. The recess forms a pocket for receiving and storing faeces, wherein the pocket's extension is defined by the edges of the recess. The article provides a simple, practical and cheap solution for handling of faeces without obviously compromising the liquid absorption properties.

18 Claims, 5 Drawing Sheets

U.S. PATENT DOCUMENTS

| | | | |
|---|---|---|---|
| 6,913,599 B2 * | 7/2005 | Mishima et al. | 604/385.08 |
| 7,204,830 B2 * | 4/2007 | Mishima et al. | 604/385.19 |
| 2003/0130643 A1 * | 7/2003 | Drevik et al. | 604/385.31 |
| 2006/0184151 A1 * | 8/2006 | Onishi et al. | 604/385.19 |

FOREIGN PATENT DOCUMENTS

| | | |
|---|---|---|
| EP | 0 659 541 B1 | 4/1998 |
| EP | 1 057 463 A2 | 12/2000 |
| EP | 1 057 464 A2 | 12/2000 |
| EP | 1 084 688 A2 | 3/2001 |
| EP | 1 086 678 A1 | 3/2001 |
| EP | 1 417 947 A1 | 5/2004 |
| ES | 2 152 433 | 2/2001 |
| JP | H06-296644 A | 10/1994 |
| JP | 08-191857 A | 7/1996 |
| JP | 2003-038553 * | 2/2003 |
| JP | 2003-038553 A | 2/2003 |
| JP | 2003038553 A * | 2/2003 |
| WO | 93/21882 A1 | 11/1993 |
| WO | WO 95/16418 A1 | 6/1995 |
| WO | WO 96/09026 A2 | 3/1996 |
| WO | 97/17920 A1 | 5/1997 |
| WO | WO 01/34082 A1 | 5/2001 |

OTHER PUBLICATIONS

PCT/ISA/210 and PCT/ISA/237 for PCT/SE2004/002027 dated Sep. 14, 2005.

Notice of Reasons for Rejection dated Jan. 26, 2010 issued in the corresponding Japanese Patent Application No. 2007-549305.

Notice of Opposition to a European Patent dated Mar. 23, 2011 issued in the corresponding European Patent No. 1845910.

* cited by examiner

ABSORBENT ARTICLE HAVING A POCKET FOR RECEIVING AND STORING FAECES AND METHOD FOR ITS MANUFACTURE

TECHNICAL FIELD

The invention relates to an absorbent article such as an incontinence shield, diaper, pant-diaper, belt diaper or similar, and a method for producing an article.

BACKGROUND

The absorbent articles of today exhibit a variety of different solutions for handling large amounts of liquid which can be excreted by the user. Superabsorbents are just one example of such a solution. Security against leakage has also been developed through the years to improve user comfort. A great problem within the field of absorbent articles, which has still not been solved in a commercially viable or comfortable manner, is the handling of faeces. Of the absorbent articles which are found on the market today, precious few present solutions for handling of faeces. This is for the simple reason that those solutions which are most often presented are as expensive as they are difficult to produce in a process. A usual speed for e.g., diaper production is from several hundred up to a thousand units per minute. Understandably, this places a heavy burden on the nature of the technical solution, which should be equally simple as cheap.

In U.S. Pat. No. 6,346,097, Blaney, a faeces container system is described. The system has a box-like form of expanded material which expands upon contact with water. The system is a separate system from the absorbent core, and therefore requires special modification of the process. Furthermore, the box-like structure expands upon secretion of urine, even though faeces are not excreted by the user. This probably means that when faeces are excreted, the box-like structure may already have expanded, and been positioned incorrectly due to the user's movements, slid out of position or quite simply collapsed under the weight of the user. A solution which is not affected by liquid but rather is only designed for faeces is therefore desirable.

Another solution for the problem of handling of faeces is described in WO97/17920, Eiterjord. Elastic threads run round an opening in the topsheet of the absorbent article, so that a cup-like shape is formed. However, the article is only designed to receive faeces. An example of this is the higher density in the central region of the article, which is obtained through, e.g., compression. This makes the article's urine-absorbing properties significantly worse in that area where they should be best. A solution which does not compromise on liquid uptake or liquid distribution properties is therefore desirable.

U.S. Pat. No. 4,642,110, Dudek, describes how a V-shaped recess, or so-called "hack", has been made in the absorbent core. The recess is intended to obtain a better fit of the diaper, in that the diaper's waist elastic gathers the whole recess together so that the absorbent core acquires a homogeneous, good-looking and accurate fit. The design requires that the absorbent core is pressed against the user. However, the document leaves the question of handling of faeces unanswered. The solution described in the document is directly unsuitable for handling of faeces as it is intended to press the absorbent core against the body of the user.

Prior to the present invention, there existed a need, therefore, for an absorbent article which provides cost-effective, practical handling of faeces, which also solves or minimizes the above problems with the previously-known solutions.

SUMMARY

Through the present invention, an absorbent article of the type described in the introduction has been provided, which article significantly removes the problems with the previously-known articles. An article according to one embodiment of the invention is primarily characterized in that a recess forms a pocket for receiving and storing of faeces, wherein the pocket's extension is defined by the edges of the recess. Optionally, the pocket may further be defined in its extension by an elastic element.

The pocket-like receiving portion exploits the volume in the absorbent article better. This is primarily through that the absorbent core is removed in the pocket, so that the space may be used for receiving and storing of faeces. It has been shown that the portion of the absorbent core which has been removed in the recess is not used to a satisfactory extent. The urine which is absorbed by the absorbent core generally lies furthest forward in the middle region, and in the front portion of an absorbent article. This phenomenon can be most easily seen when one changes the diapers of a male user.

By removing parts of the absorbent core which are anyway not used to a particularly high degree, the absorbent capacity is not appreciably worsened.

As well as the article provides a pocket for receiving and storing of faeces, the article also minimizes the comfort problem which can arise upon use of an absorbent article. Primarily, the effect which arises when the absorbent core is pressed backwards due to the user walking, running, when the article is incorrectly positioned or when the user moves in their sleep. Absorbent cores which are pressed backwards, bulges, becomes cumbersome and uncomfortable. The article adopts a shape which can be compared to a ducktail shape. The article solves this, in that a part of the absorbent core has been removed so that the material has more space to move, the article takes up less space and thereby becomes better as regards comfort. The bowl-shaped pocket provides a better fit at the same time as a pocket for receiving and storing of faeces is constructed.

The recess can take a variety of shapes. It is noted that the recess can change shape in use. Therefore, when described, the shape is considered the shape in the absorbent article's extended state, if nothing else is stated. By the article's "extended state" is meant when the article is pulled out at all its corners, so that the backsheet becomes completely taut and/or planar.

The recess can take a variety of shapes. For example, the recess can be V-shaped, U-shaped, rectangular, pyramidal, circular, ellipsoid, rhomboid, concave, convex or the like. By varying the shape of the recess, one may adjust the faeces receiving and storing properties relative to the production method and model of the absorbent article. A specific group of recesses are the rectangular, pyramidal (i.e., with the base in the direction of the article's transverse center line), circular and rhomboid recesses. These recesses generally give a larger pocket for receiving and storing of faeces.

In one embodiment, the recess is substantially V-shaped, wherein the base of the V-shaped recess lies in direct connection with the rear transverse edge of the absorbent layer. By "base of the V-shaped recess" is meant that part of the V-shape which is opposite to the tip. The tip of the V-shaped recess then points in the direction of the transverse center line of the article. In use, a V-shaped recess in the article's extended state becomes substantially convex-shaped. The user's rear/backside contributes partly to the pocket-like reception portion staying open, in that the article is taut around the rear.

One way of preventing the V-shaped recess from closing up and the pocket-like reception portion from disappearing while the article is being used is to make the angle a between the recesses' edges sufficiently large. In one embodiment, the V-shaped pocket for receiving and storing of faeces has an angle a of $\geqq 30°$, preferably $\geqq 45°$, and the length of the edges of the recess are 5-40 cm, preferably 5-20 cm, most preferably 5-15 cm. By varying the length of the recesses' edges and angle a between the recesses' edges, different sizes of the pocket for receiving and storing of faeces may be obtained.

In another embodiment, e.g., that shown in FIG. 6, the recess exhibits two angles $\alpha$ and $\beta$ between its edges. The recess then has three edges and a substantially rectangular shape in its extended state. By the shapes of the recess being rectangular, the pocket-like reception portion is prevented from closing up and disappearing when the article is used. Instead, a spacious pocket for receiving and storing of faeces is formed, by means of the recess. In another embodiment, the angles $\alpha$, $\beta$ can be varied so that $\alpha<90°<\beta$, $\alpha>90°>\beta$, or that $\alpha>90$ and $\beta>90°$ or that $\alpha<90°$ and $\beta<90°$.

In one embodiment, the elastic element which defines the extension of the pocket-like reception portion for receiving faeces comprises or consists of at least one elastic thread. However, it also lies within the scope of the invention that the elastic element can comprise 2, 3, 4, 5, 6, 7 or more elastic threads, or alternatively one or more elastic films. The elastic element is preferably arranged so as to extend substantially across the recess, between its opposing edges. The elastic element allows that the recess opposing edges are held together so that faeces do not run or are squeezed out of the recess. It also improves the pocket-like character of the recess. The elastic element may advantageously be placed in direct connection with the rear transverse edge of the absorbent core, although of course always in connection to the pocket-like reception portion. In one preferred embodiment, the elastic element is placed within 0.1-60 mm, preferably 0.1-40 mm, most preferably 0.1-20 mm from the rear transverse edge of the absorbent core. This ensures that the pocket-like reception portion maintains its pocket-like shape.

In one embodiment of an absorbent article, the article further comprises a waist elastic system connected to at least one of the article's transverse edges. The role of the waist elastic system is to hold the article in place on the user so that it does not slide off, or slide out of position. The waist elastic system can be provided in the front portion of the absorbent article or the rear portion of the absorbent article, or alternatively in both the front and the rear portions. The waist elastic system may comprise a plurality of threads which run round the entire opening of the absorbent article when the absorbent article is a diaper. In one embodiment, the waist elastic system can comprise the elastic element which defines the extension of the pocket. However, a separate elastic element may also exist which is separated from the waist elastic system as previously described.

Another way of preventing the V-shaped recess from closing up upon use of the article and the pocket-like reception portion from disappearing is to provide the recess with a length A, such as e.g., shown in FIG. 7, in the lower retention layer of preferably 5-35, preferably 10-30 cm. The recess may also have a length B in the upper retention layer of between 1-25 cm, preferably 5-20 cm.

By varying the length of the recess, various sizes and properties of the pocket for receiving and storing of faeces may be achieved. For instance, the pocket may be adjusted to suit users with large and/or frequent faeces excretions.

Naturally, an article having more recesses which comprise more pockets for receiving and storing of faeces, wherein each pocket's extension is defined by the inner edges of each recess and optionally at least one elastic element, is also within the scope of the invention. Furthermore, a pocket for receiving and storing of faeces may be located in connection with a transparent window in the backsheet. The window allows a possible carer to visually see whether a user has excreted faeces.

The absorbent core can possess two or more layers, whereby the recess extends through at least one of said sheets. In the case where the recess extends through at least two layers, the recess may have the same or different dimensions in each layer.

A method for producing an absorbent article can be carried out by providing a taut backsheet. An absorbent core having a recess is placed on the taut backsheet. In one production method, the absorbent core is glued fast to the backsheet. By the absorbent core being joined to the backsheet, formation of the pocket-like reception portion for receiving and storing of faeces is simplified. Other joining methods of the absorbent core can be ultrasonic welding, heat welding or other joining methods known in the art.

Parts of the recesses of the absorbent core are joined so that a pocket for receiving and storage of faeces is constructed. The recess can be pulled together by an elastic element being fastened in the transverse direction, the x-direction, near the rear transverse edge of the absorbent core, directly across the recess. The elastic element is fastened in its extended state to the rear transverse edge of the absorbent core and directly over the recess. When the elastic element relaxes, the sides of the recess are drawn together, and form a pocket for receiving and storage of faeces. When the backsheet is drawn together from its extended state, a fold is created in the excess backsheet material in the pocket-like reception portion, thus helping to construct the pocket. Another way is simply to physically pull the edges of the recess connected to the rear transverse edge of the absorbent core together and fasten them together with for instance a nonwoven layer.

A topsheet can be placed on the absorbent core before or after pulling together the recess, such that the absorbent core is placed between the backsheet and the topsheet.

BRIEF DESCRIPTION OF THE FIGURES

In the following, embodiments of the invention shall be more closely described with reference to the figures shown in the enclosed drawings, wherein.

DESCRIPTION OF PREFERRED EMBODIMENTS

This disclosure concerns an absorbent article such as a diaper, an incontinence shield or the like. Specifically, the disclosure concerns a faeces-receiving pocket. Among other things, the disclosure aims to provide faeces-receiving pocket which can act as a receiving pocket and storage pocket for faeces.

Figure 1:
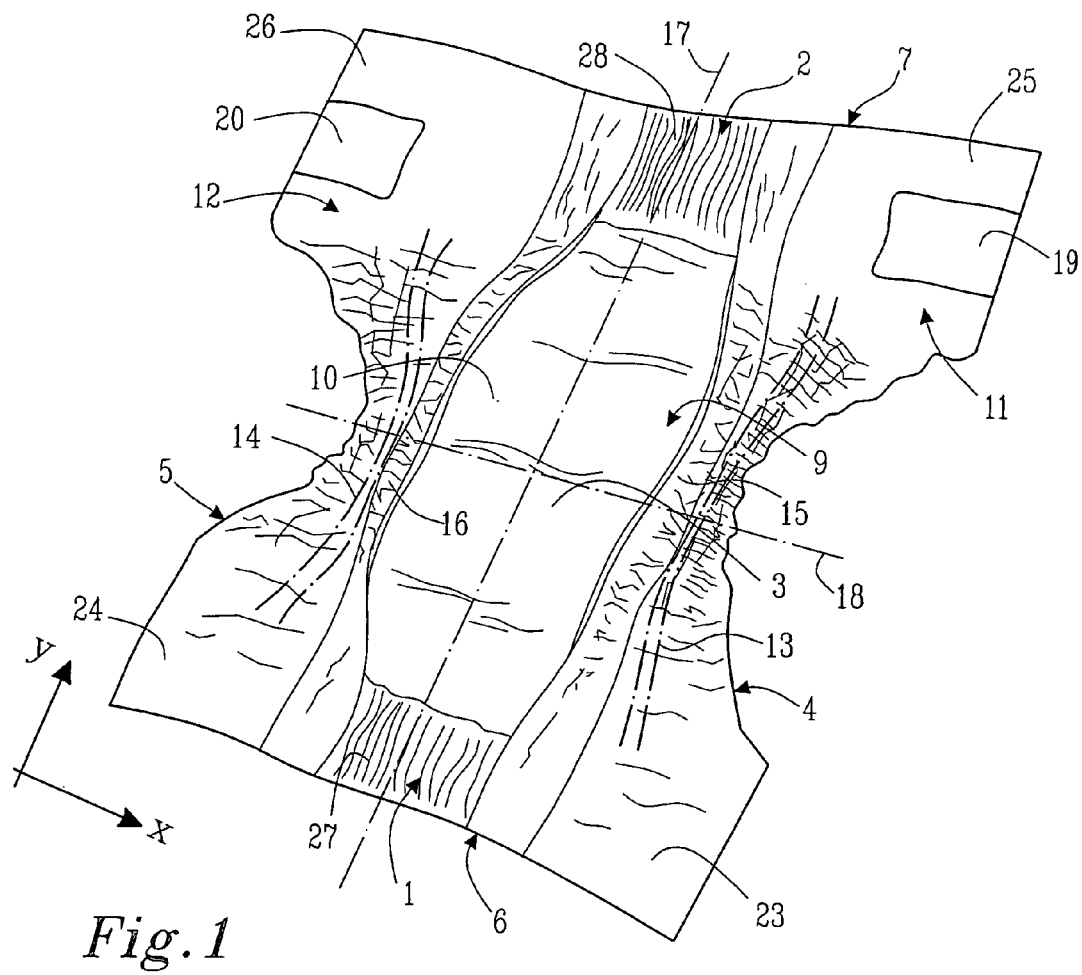
FIG. 1 shows a diaper seen from the liquid permeable topsheet.

As an example of an absorbent article, a diaper will primarily be described. The diaper has a longitudinal direction—the y-direction—with a longitudinal center line 17 and a transverse direction—the x-direction—with a transverse center line 18. In FIG. 1, a diaper is shown which comprises a front and a rear end portion 1,2, a crotch portion 3 lying therebetween, which, in use of the article, is intended to be brought between the legs of the user. The diaper further has longitudinal edges 4,5, a front transverse edge 6 and a rear transverse edge 7, a lower liquid impermeable backsheet 8, a first liquid permeable topsheet 10 and an absorbent core 9 placed therebetween. Further, the diaper possesses longitudinal leakage barriers 15,16 which run substantially parallel to the longitudinal center line 17 of the diaper and near the longitudinal edges of the absorbent core 9. The leakage barriers 15,16 contain elastic and in the figure are wrinkled together at least in their center portions.

Side flaps 11,12 extend at the sides outside the leakage barriers 15,16 and possess at least one longitudinal elastic elements 13,14 in the crotch portion 3 along their free edges. The elastic elements 13,14 serve as leg elastic upon use of the article and provide an extra leakage barrier.

The diaper also comprises fastening means 19,20 (folded towards the topsheet of the diaper in FIG. 1) in the form of hook-and-loop type fastening means; in alternative embodiments, tape with glue or other similar means may also be used. The diaper may also possess reception surfaces for said fastening means (not shown in the Figures) which are specially adapted for said fastening means.

Figure 2:
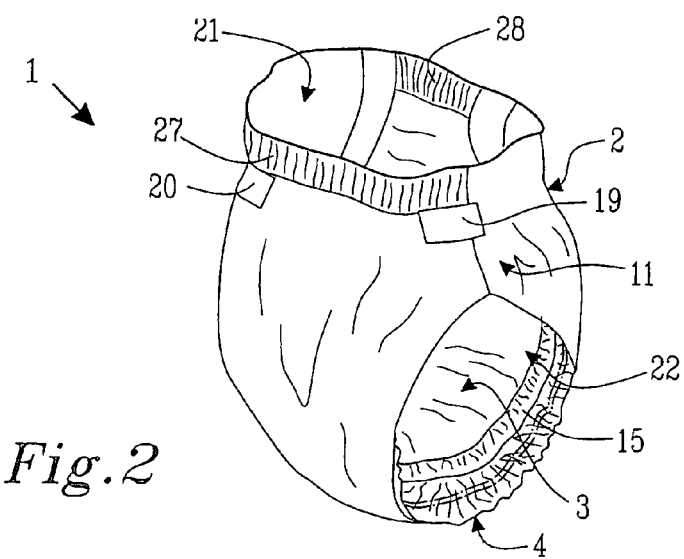
FIG. 2 shows a diaper in fastened condition in use.

The front 23,24 and rear 25,26 end regions of the side flaps 11,12 are seen at the front 1 and rear end portion 2 of the diaper. The diaper shown in FIGS. 1 and 2 has front and rear waist elastic 27,28 along at least a part of the front 23,24 and rear 25,26 end regions of the side flaps 11,12. As shown in FIGS. 1 and 2, the waist elastic 27,28 can be located on both transverse edges 6,7 of the diaper. Front and rear waist elastic 27,28 extends along roughly a third of the length of each transverse edge 6,7. In other embodiments, only a rear waist elastic may be present. Waist elastic may also exist which extends entirely along both transverse edges of the absorbent article.

FIG. 2 shows how the diaper looks during use. Here, the front end portion 1 and the rear end portion 2 of the diaper, as well as the intermediate crotch portion 3 can be seen. The front end portion 1 is connected to the rear end portion 2 via fastening means 19,20, whereby the diaper forms an upward opening for the user's trunk, and downward openings 22 for the user's legs. By the opening 22 for the user's legs, which are defined by an edge 4 on the article, namely, a portion of the side flaps 11, as well as an upright leakage barrier 15. The leakage barriers 15 are wrinkled together at least in their center portions, by elastic elements which are attached in a tensioned state to the leakage barrier 15. Alternatively, the elastic elements can be of a material which can in some way be activated, e.g., by warming, to an elasticated state. They can thereby be fastened to the support material in an unstretched, inactivated state so as to be activated afterwards to a contracted state. The elastic is tensioned under use, which leads to the leakage barrier 15 being directed up towards the user and closed tightly against the user's legs, whereby leakage is prevented.

The absorbent core 9 may comprise cellulose fibers, with or without mixing of so-called superabsorbent particles or superabsorbent fibers. However, the absorbent core may be constructed of any suitable standard material which is usually present in absorbent cores for absorbent articles such as diapers, pant-diapers, incontinence shields, panty liners and the like. The absorbent core 9 may also be constructed of more than one layer of absorbent material. Absorbent cores usually contain layers of wadding—so-called receiving and distribution layers—to be able to rapidly take away released liquid from the liquid-receiving topsheet 10. Each of the layers comprising the absorbent core may naturally contain superabsorbents. A number of absorbent cores which should be suitable in the absorbent article can be found further described in EP 659,541. Other examples of absorbent cores may be found in e.g., WO 93/21882. However, the invention is not limited to only these; rather they should only be seen as examples of absorbent cores.

The liquid-impervious backsheet 8 can comprise or consist of a liquid-impermeable plastic film, a nonwoven sheet treated with liquid-resistant material, or some other flexible material layer which has the ability to resist liquid penetration. It is usually an advantage if the liquid-impermeable backsheet 8 is breathable, i.e., allows the passage of water vapour through the sheet 8.

The liquid-permeable topsheet 9 may comprise a nonwoven sheet of e.g., polyethene fibers, polypropene fibers or mixtures thereof, perforated films or tissue layers.

Figure 3:
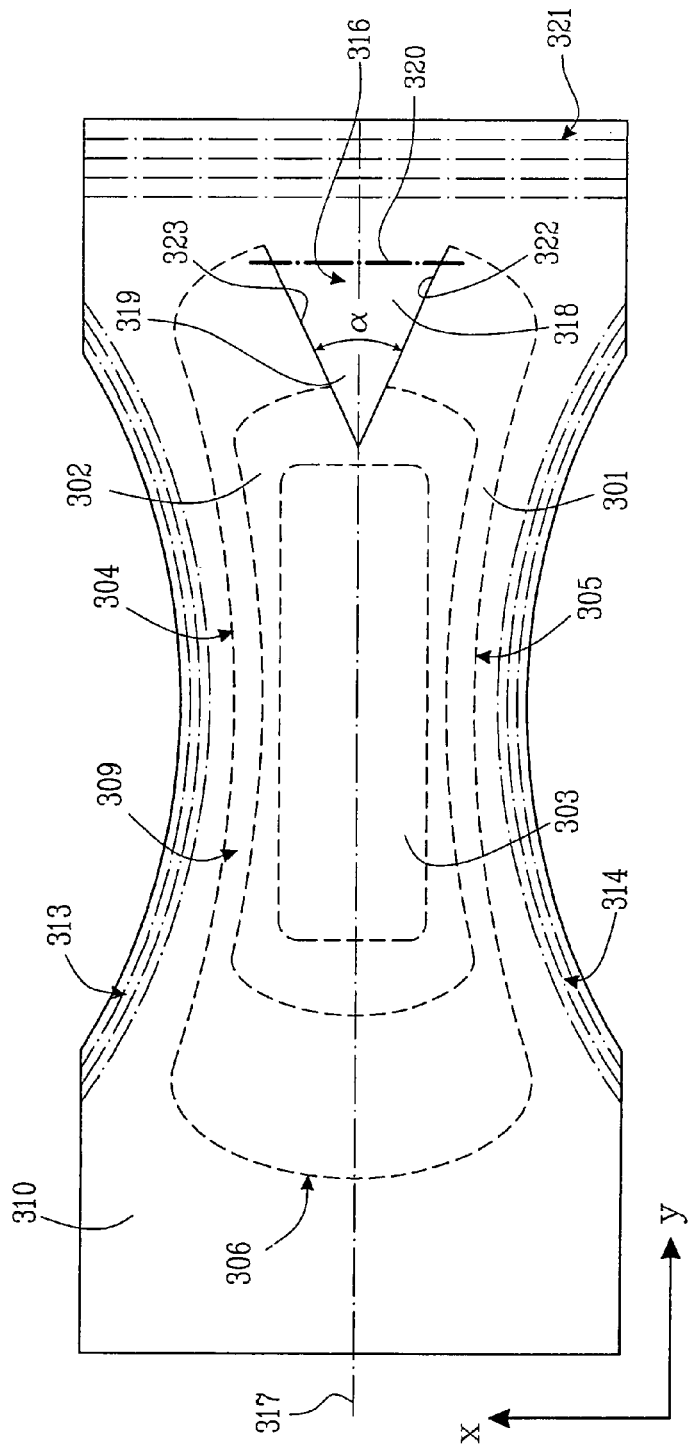
FIG. 3 shows a part of a diaper in its extended state showing a V-shaped recess in two of the layers of the absorbent core.

In FIG. 3, an absorbent core 309 is shown, seen towards the inside and with the liquid-permeable topsheet 310 in an extended state. The absorbent core 309 comprises a lower storage layer 301, an upper storage layer 302 and a liquid-distribution layer 303. The upper and lower storage layer 302, 303 are hour-glass shaped, while the liquid-distribution layer 303 is rectangular in shape. The figure also shows leg elastic 313,314 which runs substantially along the longitudinal edges of the absorbent core 9.

The absorbent core 309 has two longitudinal edges 304, 305 as well as a front and a rear transverse edge 306,307. At the transverse rear edge 307 of the absorbent core 9, the absorbent core 309 has a V-shaped recess 316. The recess 316 may be punched or cut out of the absorbent core 309, or alternatively be formed in connection with the air-laying of the absorbent core. The liquid-permeable topsheet 310 is fastened to the liquid-impermeable backsheet 308 in the recess 316 by gluing. However, other fastening methods may be applied, such as ultrasonic welding or the like.

The V-shaped recess 316 has its base in direct connection with the transverse rear edge 307 of the absorbent core 9, and its point in the direction of the transverse front edge 306 of the absorbent core. The V-shaped recess has two opposing edges 322,323 on each side of the longitudinal center line 317. The edges 322,323 of the recess 316 define the interface with the absorbent core 309. An elastic element 320 is located in close connection with the transverse rear edge 307 of the absorbent core 309, and extends across the V-shaped recess 316 between its edges 322,323, i.e., substantially in the x-direction of the article. Together with the elastic element 320 of the recess, the recess forms a pocket for receiving and storage of faeces, wherein the pocket's extension is defined by the inner edges 322,323 of the absorbent core along the recess 316 and the elastic element 320.

FIG. 3 also shows how both the lower storage layer 301 and the upper storage layer 302 possess a V-shaped recess. The V-shaped recesses are placed above one another so that only one V-shaped recess is formed. Preferably, both recesses are punched out at the same time after the storage layers 301,302 have been placed on each other.

FIG. 3 also shows the elastic element 320 of the V-shaped recess, which in the figure is comprised of a separate elastic thread 320. This elastic thread 320 is joined between the backsheet 308 and the lower storage layer 301, and in connection with the lower storage layer 301 and the rear transverse edge 307 of the absorbent core 9.

Figure 4:
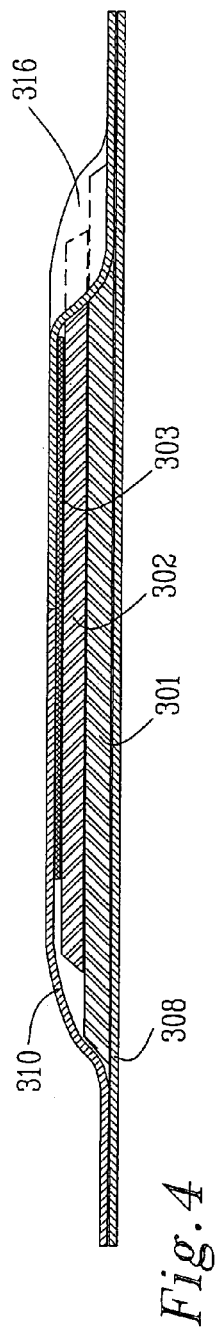
FIG. 4 shows a section view along the longitudinal center line 317 in FIG. 3.

FIG. 4 is a cross-sectional view along the longitudinal center line 317 in FIG. 3. The topsheet 310 is joined to the backsheet 308 with glue in the V-shaped recess 316. In the article's front edge, the topsheet 310 and the backsheet 308 are not joined to one another.

Figure 5:
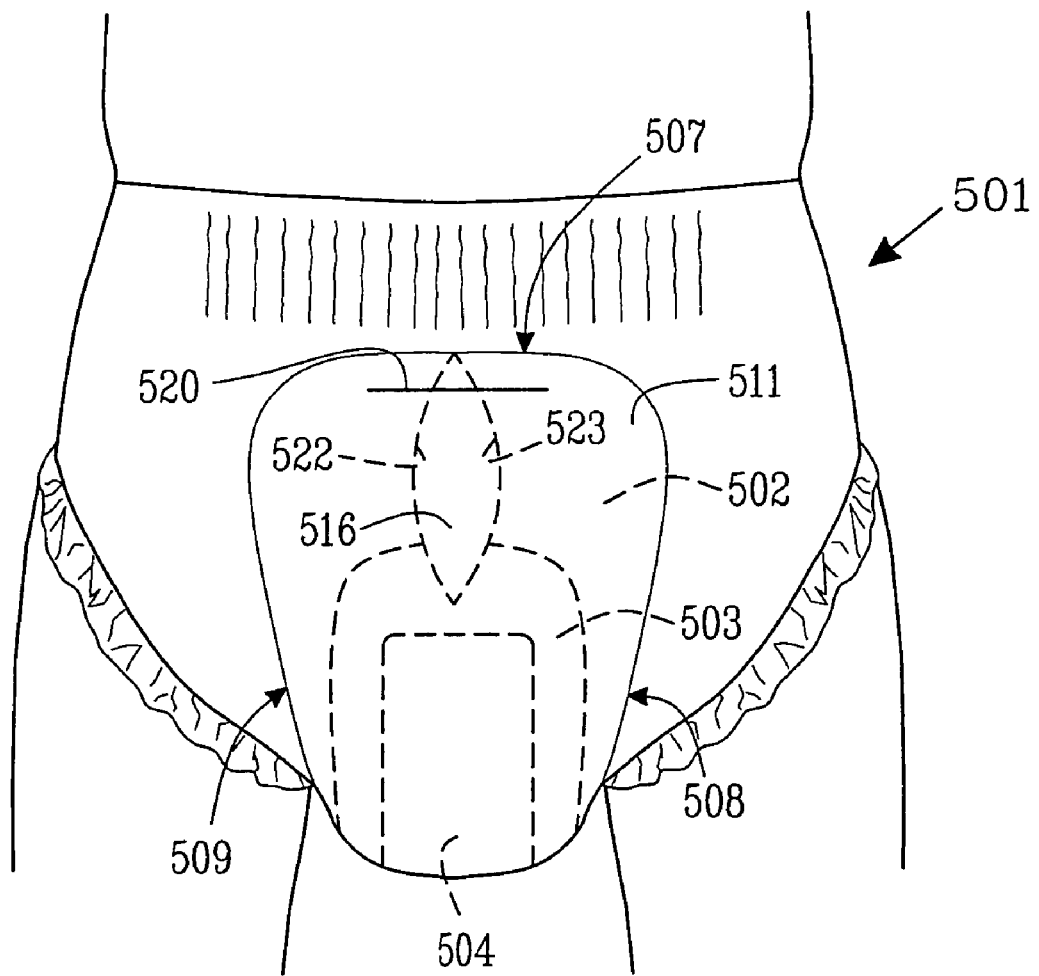
FIG. 5 shows a diaper in use according to one embodiment of the present invention.

FIG. 5 shows an absorbent article 501 in use, as viewed towards the user's backside. The contours of the lower storage layer 502, the upper storage layer 503 and the liquid distribution layer 504 are marked for the sake of clarity. The recess 516 of the absorbent core 511 is placed in the rear portion of the article, in connection with the transverse rear edge 507 of the absorbent core 511. In FIG. 5, the recess 516 has a convex form defined by the opposing edges 522,523 of the recess 516. When the article 501 is in its extended state, the recess has a substantially V-shape, as shown in FIG. 3. The recess 516 in FIG. 5 is placed substantially in the middle of the longitudinal edges 508,509 of the absorbent core 511. An elastic element 520 in the form of an elastic thread 520 contributes to the recess forming a pocket for receiving and storage of faeces. The extension of the pocket is defined, though, by the edges of the recess 522,523 and the elastic element 520.

Figure 6:
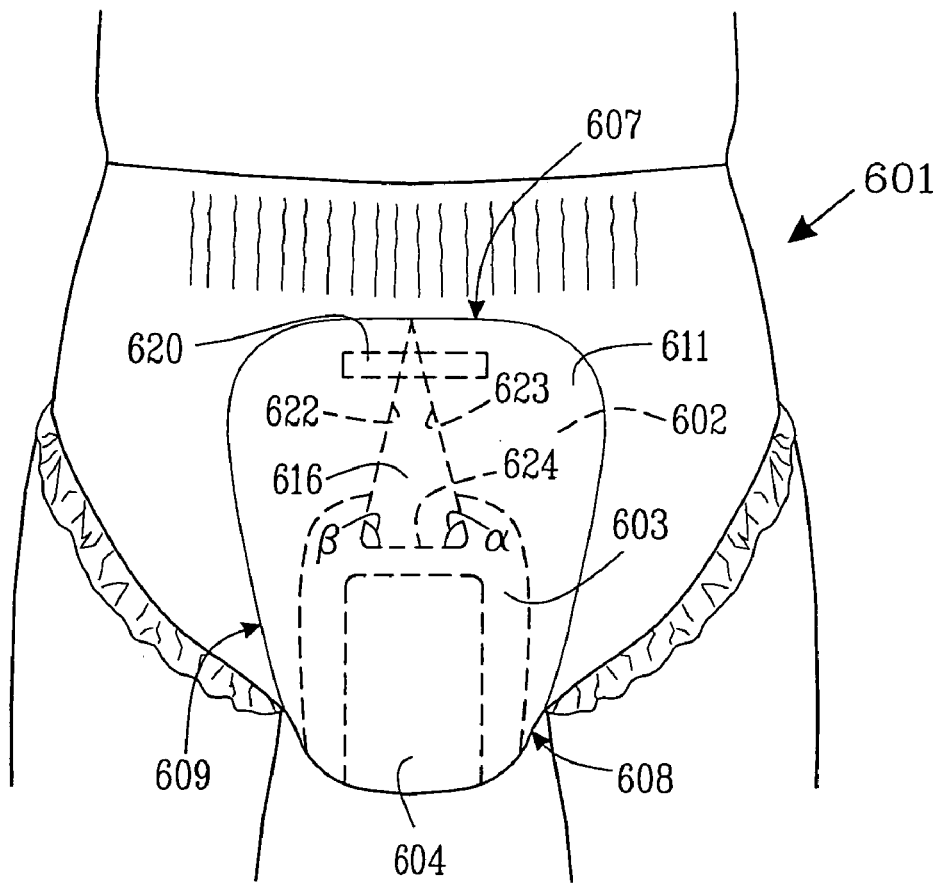
FIG. 6 shows a diaper in use according to a further embodiment of the present invention.

FIG. 6 shows another embodiment of the absorbent article 601 in use, viewed towards the backside of the user. The contours of the lower storage layer 602, the upper storage layer 603 and the liquid distribution layer 604 are marked for the sake of clarity. The recess 616 of the absorbent core 611 is placed in the rear portion of the article, in connection with the transverse rear edge 607 of the absorbent core 611. The recess 616 in FIG. 6 has a pyramidal shape, defined by the edges 622,623,624 of the recess 616. The inner edge 624 forms the base of the pyramid, and both side edges 622 and 623 the narrowing parts of the pyramid which lead to the pyramid's top. The pyramid's top is connected to the transverse rear edge 607 of the absorbent core 611. In an extended state, the recess 616 takes a substantially rectangular shape. The recess 616 in FIG. 6 is placed substantially in the middle of the absorbent core 611, between the longitudinal edges 608, 609 of the absorbent core 611. An elastic element 620, in the form of an elastic film 620 provides that the recess 616 forms a pocket for receiving and storage of faeces, whereby the extension of the pocket is defined by the edges of the recess 622, 623, 624 and the elastic element 620.

Figure 7:
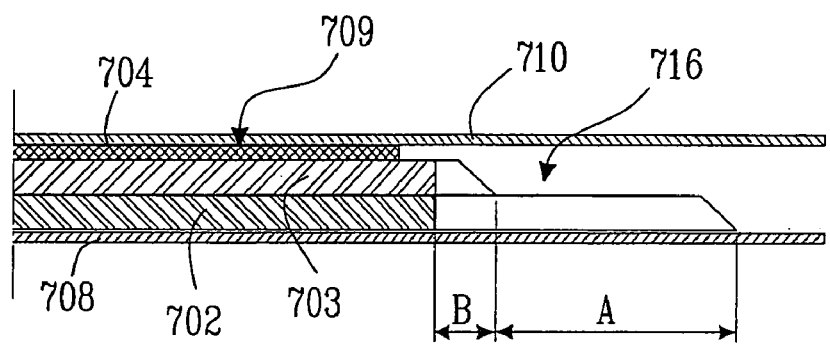
FIG. 7 shows a cross-section of part of an absorbent article with its recess in two of the layers of the absorbent core.

FIG. 7 shows an enlargement of a cross-section along a longitudinal center line of another embodiment of the invention. The absorbent article is shown in its extended state, so as to better illustrate the invention. The figure shows an absorbent core 709, a liquid permeable topsheet 710, a liquid impermeable backsheet 708; the absorbent core comprises a lower storage layer 702, an upper storage layer 703 and a liquid distribution layer 704. The absorbent core has a recess 716, wherein the recess has a length A plus B in the lower storage layer 702 and a length B in the upper storage layer 703, wherein length A is greater than length B. In the embodiment shown, length A is 25 cm and length B 10 cm. The ratio between length A in the lower storage layer 702 and length B in the upper storage layer 703 (A/B) is thus about 2.5 in the embodiment shown (a certain variation and uncertainty can arise due to error margins in the manufacturing process).

Figure 8:
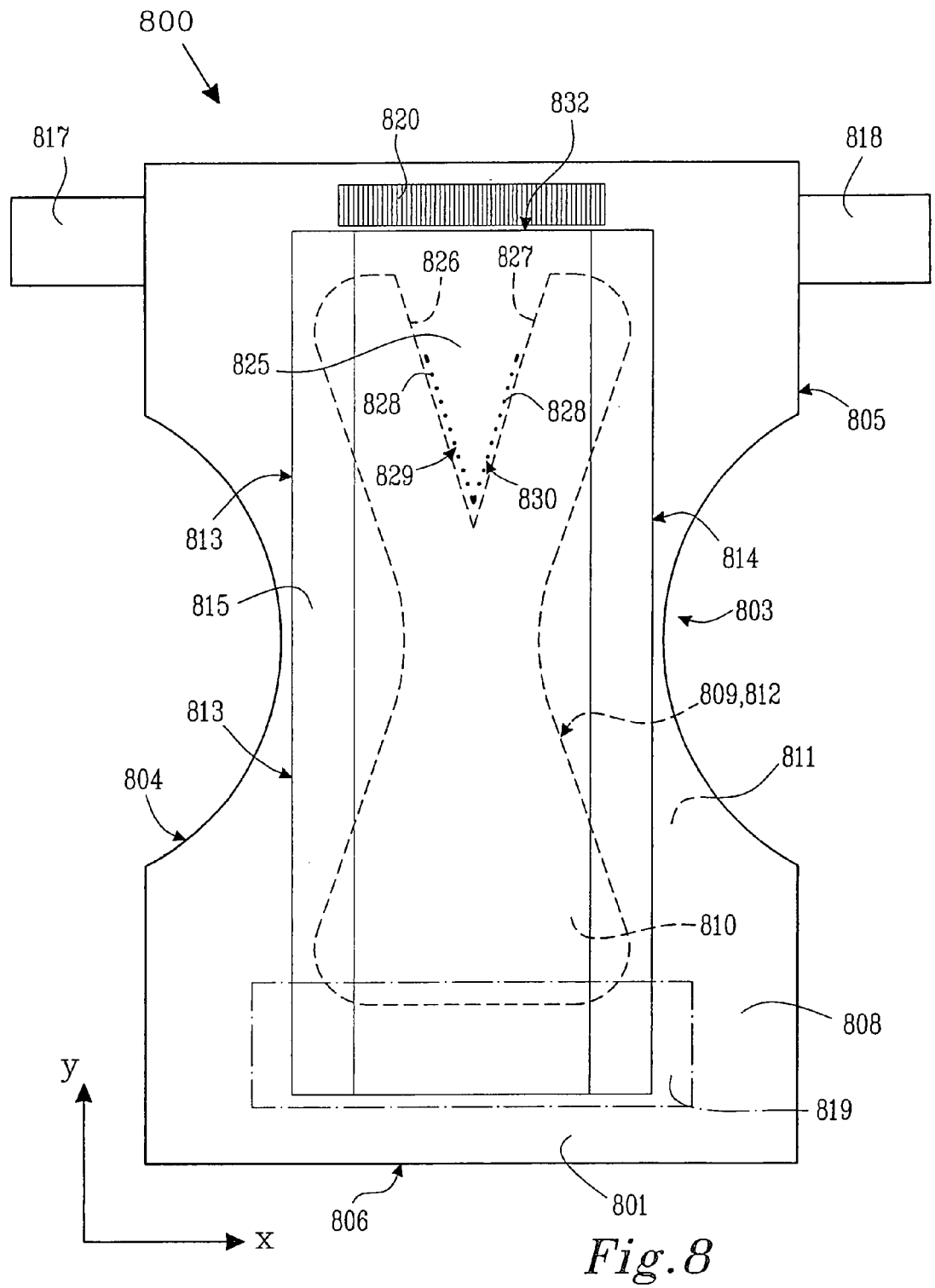
FIG. 8 shows a diaper having a recess in the absorbent core.

FIG. 8 shows a further embodiment. A diaper 800 is shown in the figure, viewed against the inside i.e., the liquid permeable topsheet 810. The diaper has a front end portion 801, a rear end portion 802 and a crotch portion 803 arranged therebetween. The diaper 800 has two longitudinal edges 804, 805, and a front transverse edge 806 and a rear transverse edge 807. The diaper has a backsheet 808, upon which an absorbent packet 809 is arranged. The absorbent packet 809 comprises a liquid permeable topsheet 810, a breathable—yet liquid impervious—backsheet 811 and a absorbent core 812 placed therebetween. Upright leakage barriers 815,816 are arranged on the liquid permeable topsheet 810 in a longitudinal direction and in connection with the longitudinal edges 813,814 of the absorbent packet 810. The upright leakage barriers 815,816 extend along the whole length of the absorbent packet 809.

The absorbent packet 809 is fastened to the backsheet 808 with the help of glue or ultrasonic welds. The whole absorbent packet 809, or alternatively only portions of the absorbent packet 809 may be fastened. For example the absorbent packet 809 can be fastened by the corners of the absorbent packet 809 to the backsheet 808, or along two or more edges of the absorbent packet 809. When only two edges of the absorbent packet 809 are fastened to the backsheet 808, it is preferably the two transverse edges which are fastened, or alternatively only the two longitudinal edges which are fastened.

Diaper 800 also has a fastening means in the form of two hook-tabs 817, 818 which are placed on the rear end portion 802 of the diaper, together with a loop zone 819 placed on the diaper's front end portion 801. Waist elastic 820 in the form of an elastic film is placed in the rear end portion 802 in connection with the rear transverse edge 807.

The absorbent core 812 has a V-shaped recess 825 in the diaper's rear end portion 802 which forms a pocket for receiving and storage of faeces. Along the edges of the recess, the liquid-permeable topsheet 810 is joined to the liquid-impermeable backsheet 811 by ultrasonic welds in the form of small points 828. The ultrasonic welds 828 together form two weld-lines 829, 830 which help to maintain the recess 825 of the absorbent core 812 intact so that the pocket for receiving and storage of faeces does not collapse. Weld-lines are of most use when the recess 825 is V-shaped. With recesses of other shapes, the need for such weld-lines becomes significantly lower. The point-wise ultrasonic welds 828 may alternatively be formed from welded long lines. Weld-lines 829, 830 only extend along half of the V-shaped recesses' 825 edges 826,827, but may of course extend further in other embodiments. An elastic element 831 extends along the transverse rear edge 832 of the absorbent packet 809. The elastic element 831 is fastened to the absorbent packet 809 in its extended state so that, upon relaxation of the elastic element 831, a pocket for receiving and storage of faeces 825 is formed. Alternatively, the elastic element 831 is of a material which can be activated, as described above, which can be fastened to the absorbent core in an inactivated state so as to be activated later to a contracted elastic state.

It should be noted that the described features of the various embodiments may be combined with each other; accordingly, no embodiment is intended to limit any combination of features which are presented in the embodiments, but rather only to illustrate examples of embodiments.

What is claimed is:

1. An absorbent article comprising:
   a topsheet, a backsheet and an absorbent core placed therebetween, a front and a rear transverse edge, two longitudinal edges, and a transverse center-line which divides the article into a front end portion adapted to lie adjacent to or in contact with a wearer's abdomen when in use, and a rear end portion adapted to lie adjacent to or in contact with the wearer's backside when in use, said absorbent core having two longitudinal edges, a front transverse edge, and a rear transverse edge, wherein the rear transverse edge of the absorbent core possesses a recess with at least one pair of opposing edges, the recess forms a pocket for receiving and storing faeces deposited in the article's rear end portion, the pocket's extension is defined by the edges of the recess, and the topsheet of the absorbent article is fixed to the backsheet in the recess, and an elastic element is arranged to extend substantially across the recess between its opposing edges in a direction parallel to the transverse centerline of the article, the elastic element directly attached to the opposing edges of the recess.

2. The absorbent article according to claim 1, wherein the recess is V-shaped when the article is in an extended state.

3. The absorbent article according to claim 2, wherein a base of the V-shaped recess lies in direct connection with the rear transverse edge of the absorbent core and a tip of the V-shaped recess points in a direction of the article's transverse center-line.

4. The absorbent article according to claim 3, wherein an angle between the edges of the recess is $\geq 30°$ and a length of the edges of the recess is $\geq 5$ cm.

5. The absorbent article according to claim 1, wherein the elastic element comprises at least one elastic thread.

6. The absorbent article according to claim 1, wherein the elastic element is connected to the rear transverse edge of the absorbent core.

7. The absorbent article according to claim 6, wherein the elastic element is located within 0.1-10 mm from the rear transverse edge of the absorbent core.

8. The absorbent article according to claim 1, wherein the absorbent article further comprises a waist elastic system connected to at least one of the article's transverse edges.

9. The absorbent article according to claim 8, wherein the waist elastic system is located in the rear end portion of the article.

10. The absorbent article according to claim 1, wherein the recess has a substantially convex shape when the article is in an extended state.

11. The absorbent article according to claim 1, wherein the recess has a substantially rectangular shape when the article is in an extended state.

12. The absorbent article according to claim 1, wherein the recess has a substantially circular shape when the article is in an extended state.

13. The absorbent article according to claim 1, wherein the absorbent core has two or more layers, and the recess extends through at least one of said layers.

14. The absorbent article according to claim 13, wherein the recess extends through at least one of said layers, and the recess has the same or different dimensions in each layer.

15. The absorbent article according to claim 1, wherein the elastic element is disposed between the topsheet and the backsheet.

16. The absorbent article according to claim 1, wherein the recess is configured such that the opposing edges of the recess at the rear transverse edge of the absorbent core are drawn towards each other via the elastic element when the absorbent article is secured to the wearer.

17. The absorbent article according to claim 1, wherein the absorbent core includes an upper storage layer and a lower storage layer, and the elastic element is joined between the backsheet and the lower storage layer.

18. An absorbent article comprising:

a topsheet, a backsheet and an absorbent core placed therebetween, a front and a rear transverse edge, two longitudinal edges, and a transverse centerline which divides the article into a front end portion adapted to lie adjacent to or in contact with a wearer's abdomen when in use, and a rear end portion adapted to lie adjacent to or in contact with the wearer's backside when in use, said absorbent core having two longitudinal edges, a front transverse edge, and a rear transverse edge, wherein the rear transverse edge of the absorbent core possesses a recess with at least one pair of opposing edges, the recess forms a pocket for receiving and storing faeces deposited in the article's rear end portion, the pocket's extension is defined by the edges of the recess, and the topsheet of the absorbent article is fixed directly to the backsheet in the recess, and an elastic element is arranged to extend substantially across the recess between its opposing edges in a direction parallel to the transverse centerline of the article, the elastic element directly attached to the opposing edges of the recess.

* * * * *